United States Patent
Kanazawa

(10) Patent No.: US 7,623,901 B2
(45) Date of Patent: Nov. 24, 2009

(54) MAGNETIC RESONANCE IMAGING NEEDING A LONG WAITING TIME BETWEEN PRE-PULSES AND IMAGING PULSE TRAIN

(75) Inventor: Hitoshi Kanazawa, Utsunomiya (JP)

(73) Assignee: Kabushiki Kaisha Toshiba, Minato-Ku, Tokyo (JP)

( * ) Notice: Subject to any disclaimer, the term of this patent is extended or adjusted under 35 U.S.C. 154(b) by 268 days.

(21) Appl. No.: 10/416,451

(22) PCT Filed: Nov. 15, 2001

(86) PCT No.: PCT/JP01/09997

§ 371 (c)(1),
(2), (4) Date: Sep. 12, 2003

(87) PCT Pub. No.: WO03/041579

PCT Pub. Date: May 22, 2003

(65) Prior Publication Data

US 2004/0049106 A1    Mar. 11, 2004

(51) Int. Cl.
*A61B 5/05* (2006.01)
(52) U.S. Cl. .................. 600/413; 600/410
(58) Field of Classification Search .............. 600/413, 600/410
See application file for complete search history.

(56) References Cited

U.S. PATENT DOCUMENTS 5,000,182 A * 3/1991 Hinks .................... 600/413
5,781,010 A * 7/1998 Kawasaki et al. ........ 324/309
6,498,946 B1 * 12/2002 Foo et al. ................. 600/410

FOREIGN PATENT DOCUMENTS

| EP | 0 412 695 A2 | 2/1991 |
|---|---|---|
| JP | 60-215352 A | 10/1985 |
| JP | 2-60635 A | 3/1990 |
| JP | 3-131238 A | 6/1991 |
| JP | 9-238916 A | 9/1997 |

OTHER PUBLICATIONS

European Search Report dated Jun. 14, 2005.
Simonetti et al., "'Black Blood', T2-Weighted Inversion-Recovery MR Imaging of the Heart", Radiology, vol. 199, No. 1, 49-57, Apr. 1996.

* cited by examiner

*Primary Examiner*—Long V Le
*Assistant Examiner*—Jacqueline Cheng
(74) *Attorney, Agent, or Firm*—Nixon & Vanderhye PC

(57) ABSTRACT

In the black blood method using a double inversion pulse, images in the systole of the cardiac cycle can be captured in a reliable manner even in the presence of a cycle-to-cycle variance in the heart beat cycle. A pulse sequence of the black blood method composed of a double inversion pulse DIV and an imaging pulse train $SEQ_{ima}$ is used. This sequence is applied in sync with an ECG signal of a subject to be imaged, and magnetic resonance imaging is thereby performed. The double inversion DIV is applied in sync with an R-wave:R1 appearing on the ECG signal at a given timing, with a first delay time td1 (fixed value), and the imaging pulse train $SEQ_{ima}$ is applied in sync with the following R-wave:R2 with a second delay time td2 (fixed value: set in accordance with the systole). A variance of the cardiac cycle is absorbed in an inversion time BBTI.

27 Claims, 9 Drawing Sheets

BBTI2 < BBTI1

MAGNETIC RESONANCE IMAGING NEEDING A LONG WAITING TIME BETWEEN PRE-PULSES AND IMAGING PULSE TRAIN

TECHNICAL FIELD

The present invention relates to magnetic resonance imaging (MRI) for imaging the internal of a subject to be imaged with an imaging sequence containing a pre-pulse, and more particularly to MR imaging using an imaging sequence in which a waiting time until the application of an imaging pulse train is started after a pre-pulse was applied is relatively long in comparison with a cardiac cycle as with the black blood method or the like.

BACKGROUND ART

Magnetic resonance imaging is presently used in many cases as one of imaging methods for medical use. Magnetic resonance imaging is an imaging method that gives rise to magnetic excitation of nuclear spins in a subject to be imaged positioned in a static magnetic field with a high frequency signal at the Larmor frequency and then reconstructs an image of the internal of the subject to be imaged using an MR signal induced in association with the excitation. Magnetic resonance imaging includes various types, and the type is also divided according to pulse sequences used for magnetic excitation and signal acquisition.

In the case of magnetic resonance imaging for imaging a region in the heart, ghost-like artifacts (blood flow artifacts) readily appear on a reconstructed image in a phase-encoding direction from a portion where a number of blood flows are present due to influences of a pulse beat of blood. In order to suppress the artifacts, the cardiac synchronization imaging method is generally used, by which RF excitation and echo acquisition are synchronized with electrocardiographic waveforms. According to this method, a variance of an echo signal occurring in each shot (excitation) can be suppressed, and the aforementioned blood flow artifacts can be thereby reduced.

Also, as one can review in articles, Edelman RR et al., "Fast selective black blood MR imaging", *Radiology* 1991 December 181(3): 655-60, 1991, Edelman RR et al., "Extracranial carotid arteries: evaluation with "black blood"MR angiography", *Radiology* 1990 October 177(1): 45-65, 1990, etc., with the aim at chiefly improving a capability of extracting the cardiac muscle, a so-called black blood method has been proposed, by which a pre-pulse used to suppress the acquisition of an MR signal of blood is appended to the front of a pulse train for normal RF excitation and echo acquisition. As for a pulse train for the RF excitation and the echo acquisition, a pulse train through the field echo method, the fast field echo method, the fast spin echo method, etc. is used as the pulse train.

Moreover, there has been recently reported the black blood method using a so-called double inversion pulse, by which a selective inversion pulse that gives rise to inversion excitation in a region substantially the same as the imaging plane and a non-selective inversion pulse that gives rise to inversion excitation in the whole subject to be imaged are successively applied, and the RF excitation and the echo acquisition for imaging are performed 400 to 700 ms later from this application (see articles, for example, Simonetti OP et al., ""Black Blood" T2-weighted inversion-recovery MR imaging of the heart", *Radiology* 1996 April 199(1): 49-57,1996, Stehling MK et al., "Single-shot T1- and T2-weighted magnetic resonance imaging of the heart with black blood: preliminary experience", *MAGMA* 1996 September December, 4(3-4): 231-40, 1996, Arai AE et al., "Visualization of aortic valve leaflets using black blood MRI", *J Magn. Reson. Imaging* 1999 November, 10(5): 771-7, 1999, etc.)

The black blood method using the double inversion pulse attracts the attention because of its advantages that a suppressing effect of a blood signal is high and deterioration in signals of other tissues is small, and is expected to become increasingly more popular. The shape of the pre-pulse varies from report to report. Because the pre-pulse is basically intended to reduce the longitudinal magnetization of a blood signal to a null point or to a sufficiently small level, a time from the application of the pre-pulse to the application of an excitation pulse for imaging is approximately 400 to 700 ms in all the reports, which is longer than in the case of a pre-pulse applied for other purposes.

For this reason, even when the pre-pulse is applied immediately after the detection of an R-wave through the use of the cardiac synchronization imaging method, cardiac temporal phases that can be actually imaged are those in a time zone in the latter half of the cardiac cycle, that is, in the diastole. Hence, as one can review in the article supra, Simonetti Op et al., ""Black Blood" T2-weighted inversion-recovery MR imaging of the heart", *Radiology* 1996 April 199(1): 49-57, 1996, it is general to acquire images in the diastole when this black blood method is used.

A pulse sequence of the conventional black blood method using the double inversion pulse is shown in FIG. 1. As shown in the drawing, a double inversion pulse DIV as the pre-pulse for blood suppression is applied in sync with an ECG (electrocardiogram) signal with a predetermined time td from an R-wave thereof, then an imaging pulse train $SEQ_{ima}$ is applied when a predetermined waiting time BBTI has elapsed since this application, where by echo signals are acquired. In the drawing, RF indicates an RF pulse, Gs indicates a slicing direction gradient magnetic field, Gr indicates a readout direction gradient magnetic field, Ge indicates a phase-encoding direction gradient magnetic field, and Echo indicates an echo signal.

Of the two RF pulses of the double inversion pulse DIV, one is applied with the slicing direction gradient magnetic field Gs of a zero strength, and the other is applied with the slicing direction gradient magnetic field Gs of a necessary strength in order to give rise to excitation in a region same as the slice subjected to selective excitation with a pulse sequence for imaging. The waiting time BBTI is approximately 500 to 600 ms in general, and is set to a time at which the longitudinal magnetization of blood is reduced to or nearly to a null point.

However, when the conventional black blood method is used, there arise problems that images in the systole near an R-wave on time are difficult to acquire, and it is difficult to acquire a series of images having latencies that vary at regular intervals as with a cine mode display.

Because a long time:BBTI (inversion time of the black blood method) is needed from the application of the pre-pulse to the echo acquisition, in order to acquire images in the systole, an R-wave in the last or earlier cardiac cycle with respect to a cardiac cycle from which images are actually acquired has to be used as a synchronous trigger. This state is shown in FIG. 2. That is, as shown in the drawing, in order to acquire images in the systole from R2 to R3, synchronization has to be made with an R-wave:R1 with a predetermined delay time td in the earlier cardiac cycle, for example, in the cardiac cycle from R1 to R2.

The cycle of heartbeats varies by 10 to 20% even in a normal healthy subject. That is, the position of an R-wave is displaced on the time axis in every heartbeat. Hence, even when images are acquired after a certain time "td+BBTI" from an R-wave in the last or earlier cardiac cycle, the position of the cardiac muscle at the time instance of the echo acquisition sways in each shot, which deteriorates the image quality so badly that it is impossible to obtain an image that can be used for a diagnosis. FIG. 3A and FIG. 3B are views schematically showing FIG. 2 divided by two conditions of a long cardiac cycle (FIG. 3A) and a short cardiac cycle (FIG. 3B). As shown in FIG. 3A and FIG. 3B, in a conventional case, the start timing of an imaging pulse train $SEQ_{ima}$ is controlled by fixing a delay time td1 and an inversion time BBTI, which causes a delay time td2 having a strong correlation with actual motions of the cardiac muscle to vary in the same manner as the cardiac cycle varies.

For this reason, as has been described above, it is the images in the diastole alone that can be acquired in the conventional method.

The invention was devised to break through the current situation of the foregoing related art, and therefore, has an object to provide an imaging method capable of capturing images in the systole of the cardiac cycle in a reliable manner, even in the presence of a cycle-to-cycle variance of the cardiac cycle, in MR imaging using a pulse sequence in which a waiting time until the application of an imaging pulse train after a pre-pulse was applied is relatively long in comparison with the cardiac cycle like the imaging through the black blood method using a double inversion pulse.

DISCLOSURE OF THE INVENTION

In order to achieve the above and other objects, according to magnetic resonance imaging of the invention, synchronization is applied to a pre-pulse and an imaging pulse train of a pulse sequence respectively with a plurality of specific waveforms (for example, R-waves) lined on the time series of a signal (for example, an ECG signal) representing cardiac temporal phases.

To be more specific, according to one aspect of the invention, in a magnetic resonance imaging apparatus that applies a pre-pulse to a subject to be imaged, and then performs scanning by applying an imaging pulse train to a desired region of said subject to be imaged when a desired standby time has elapsed since said pre-pulse was applied, it is characterized in that said apparatus comprises: acquiring means for acquiring a signal representing cardiac temporal phases of said subject to be imaged; pre-pulse applying means for applying said pre-pulse in sync with a specific waveform appearing on the signal acquired by said acquiring means at a given timing, with a first delay time; and scanning means for performing scanning by applying said imaging pulse train in sync with said specific waveform appearing on the signal detected by said acquiring means at a timing at least one cardiac cycle later than said timing, with a second delay time.

For example, said pre-pulse is a double inversion pulse that forms part of a pulse sequence through a black blood method. Also, for example, said signal representing the cardiac temporal phases is an ECG signal, and said specific waveform is an R-wave of said ECG signal. Further, for example, said timing at least one cardiac cycle later at which said scanning means starts the scanning is a timing at which one cardiac cycle or two cardiac cycles have elapsed.

Also, it is characterized in that said predetermined standby time is long enough to account for approximately a half or more than the half of one cycle of heart beat.

Further, it is preferable that said second delay time is a time set in accordance with a systole of heart beat, and said first delay time is a time calculated using said second delay time, a desired value of said standby time, and an average cycle of heart beat.

Also, according to another aspect of the invention, in a magnetic resonance imaging apparatus that applies a pre-pulse to a subject to be imaged, and then performs scanning by applying an imaging pulse train to a desired region of said subject to be imaged when a predetermined standby time has elapsed since said pre-pulse was applied, it is characterized in that said apparatus comprises means for synchronizing applications of said pre-pulse and said imaging pulse train respectively with two waveforms of the same kind appearing at different timings on a signal representing cardiac temporal phases of said subject to be imaged.

According to still another aspect of the invention, in a scanning synchronization method of magnetic resonance imaging for applying a pulse sequence for magnetic resonance imaging, composed of a pre-pulse and an imaging pulse train whose application is started at a time instant at which a desired standby time has elapsed since said pre-pulse was applied, to a subject to be imaged in sync with a signal representing cardiac temporal phases of said subject to be imaged, it is characterized in that: said pre-pulse is applied in sync with a specific waveform appearing on said signal at a given timing, with a first delay time; and scanning is performed by applying said imaging pulse train in sync with said specific waveform appearing on said signal at a timing at least one cardiac cycle later than said timing, with a second delay time.

Further, in the invention, it is possible to provide a computer-readable recoding medium used for magnetic resonance imaging for applying a pulse sequence for magnetic resonance imaging composed of a pre-pulse and an imaging pulse train to a subject to be imaged in sync with a signal representing cardiac temporal phases of said subject to be imaged, said recording medium recording a program that causes a computer to perform: a function of applying said pre-pulse in sync with a specific waveform appearing on said signal at a given timing, with a first delay time; and a function of performing scanning by applying said imaging pulse train in sync with said specific waveform appearing on said signal at a timing at least one cardiac cycle later than said timing, with a second delay time.

Furthermore, it is possible to provide a program for magnetic resonance imaging for applying a pulse sequence for magnetic resonance imaging composed of a pre-pulse and an imaging pulse train to a subject to be imaged in sync with a signal representing cardiac temporal phases of said subject to be imaged, said program causing a computer to perform: a function of applying said pre-pulse in sync with a specific waveform appearing on said signal at a given timing, with a first delay time; and a function of performing scanning by applying said imaging pulse train in sync with said specific waveform appearing on said signal at a timing at least one cardiac cycle later than said timing, with a second delay time.

According to the invention, synchronization can be applied to a pre-pulse and an imaging pulse train that form a pulse sequence in the black blood method or the like respectively with different, specific waveforms (R-waves or the like) of a signal (ECG signal or the like) representing cardiac temporal phases of a subject to be imaged with different delay times. It is thus possible to maintain a regular application timing of an imaging pulse train for acquiring echo signals always even in the presence of a variance of the cardiac cycle. Consequently, in MR imaging using a pulse sequence in which a waiting time between the pre-pulse and the imaging pulse train is long in comparison with the cardiac cycle, images in the systole of the cardiac cycle can be captured in a reliable manner even in the presence of a cycle-to-cycle variance of the cardiac cycle. It is thus possible to improve the image quality of an MR image by reducing the artifacts.

It should be noted that, in the imaging through the black blood method according to the magnetic resonance imaging of the invention, a time BBTI from the application of the pre-pulse to the application of the imaging pulse train is relatively long in comparison with one cardiac cycle, and a difference of the suppressing effect of a blood signal due to a variance of the BBTI within a range from approximately 400 to 700 ms is so small that the influence on the image quality is almost negligible.

BEST MODE FOR CARRYING OUT THE INVENTION

The following description will describe one embodiment of the invention with reference to FIG. 4 through FIG. 6, FIG. 7A, and FIG. 7B.

Figure 1:
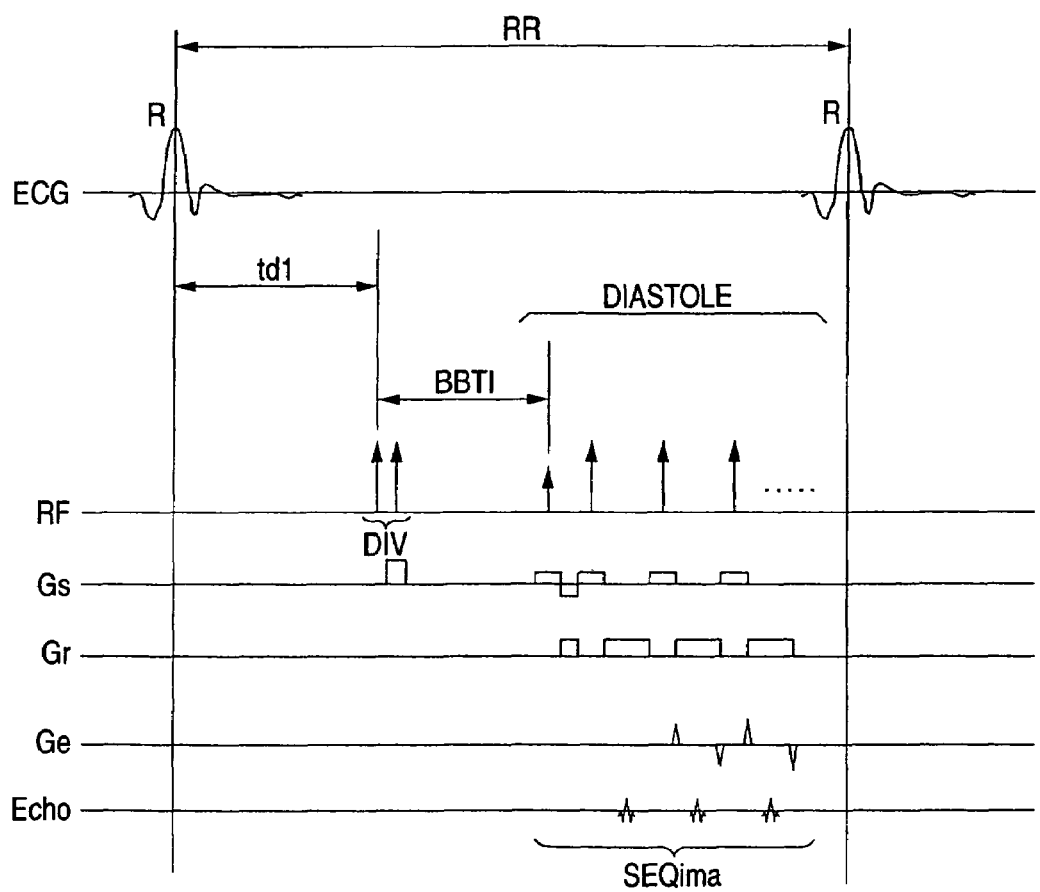
FIG. 1 illustrates a pulse sequence showing the conventional black blood method.
Figure 2:
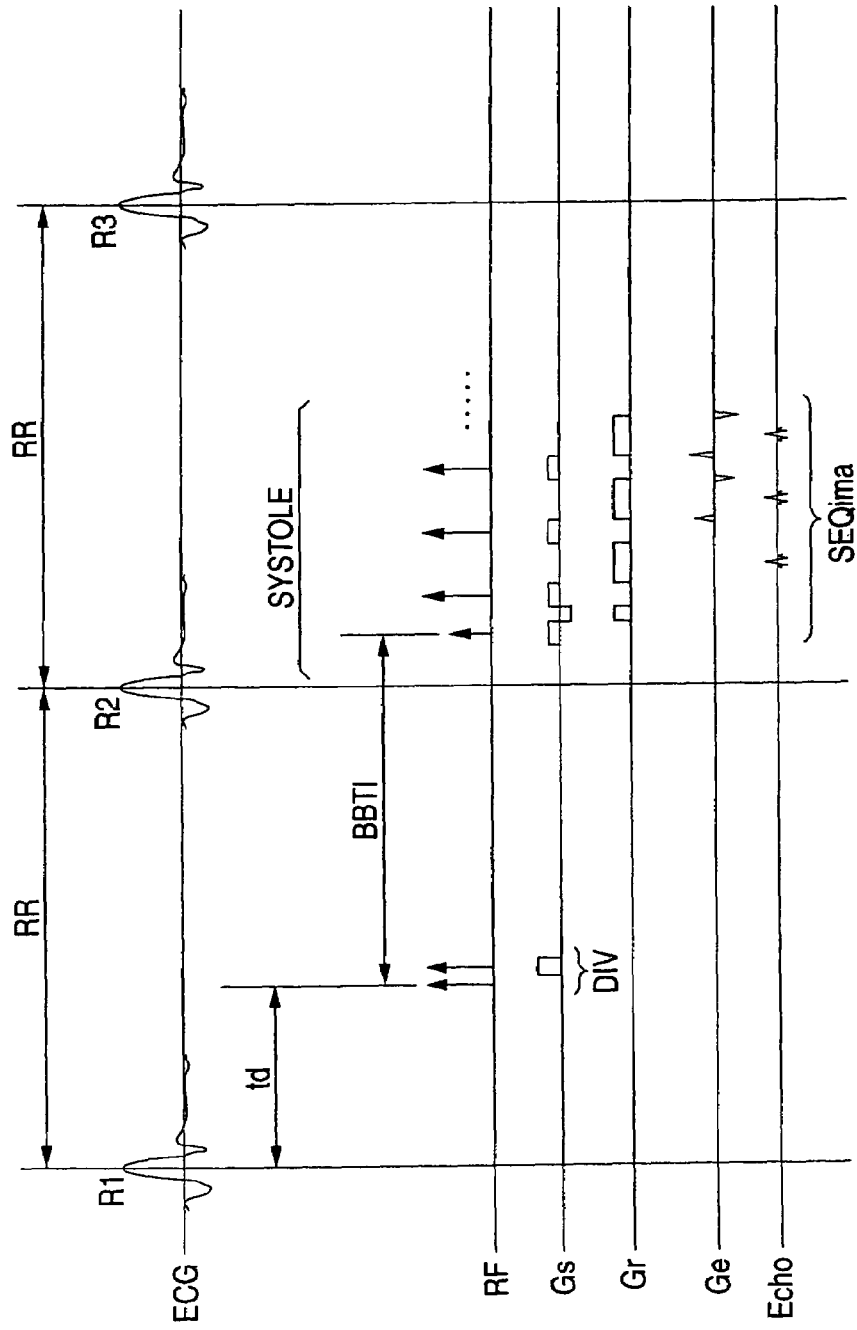
FIG. 2 illustrates a pulse sequence showing one example of a synchronization method through the conventional black blood method.
Figure 3A:
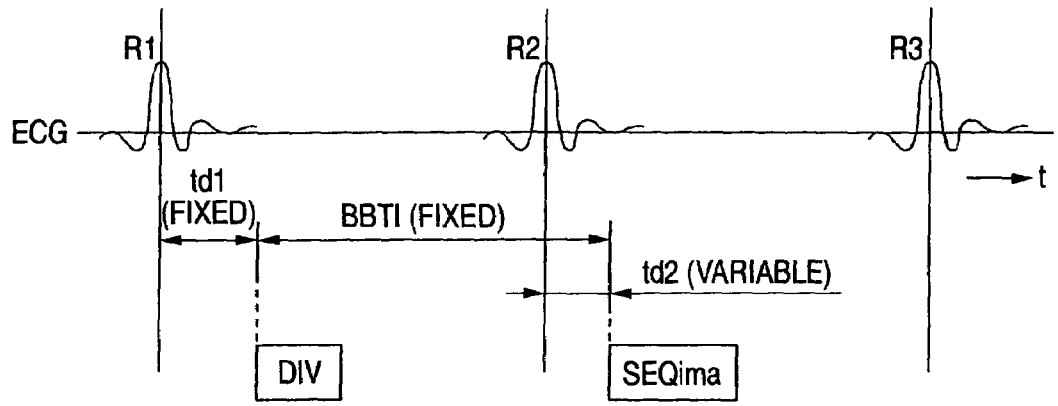
FIG. 3A and FIG. 3B illustrate pulse sequences used to explain an inconvenience of the synchronization method through the conventional black blood method.
Figure 3B:
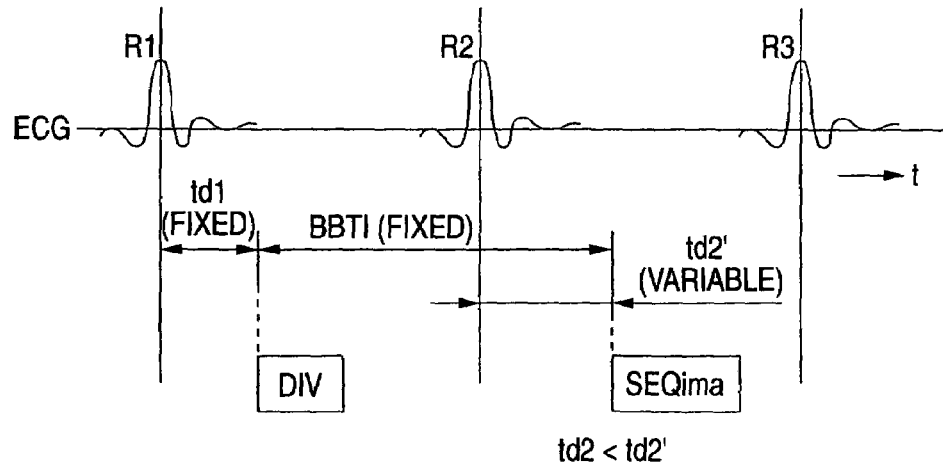
Figure 4:
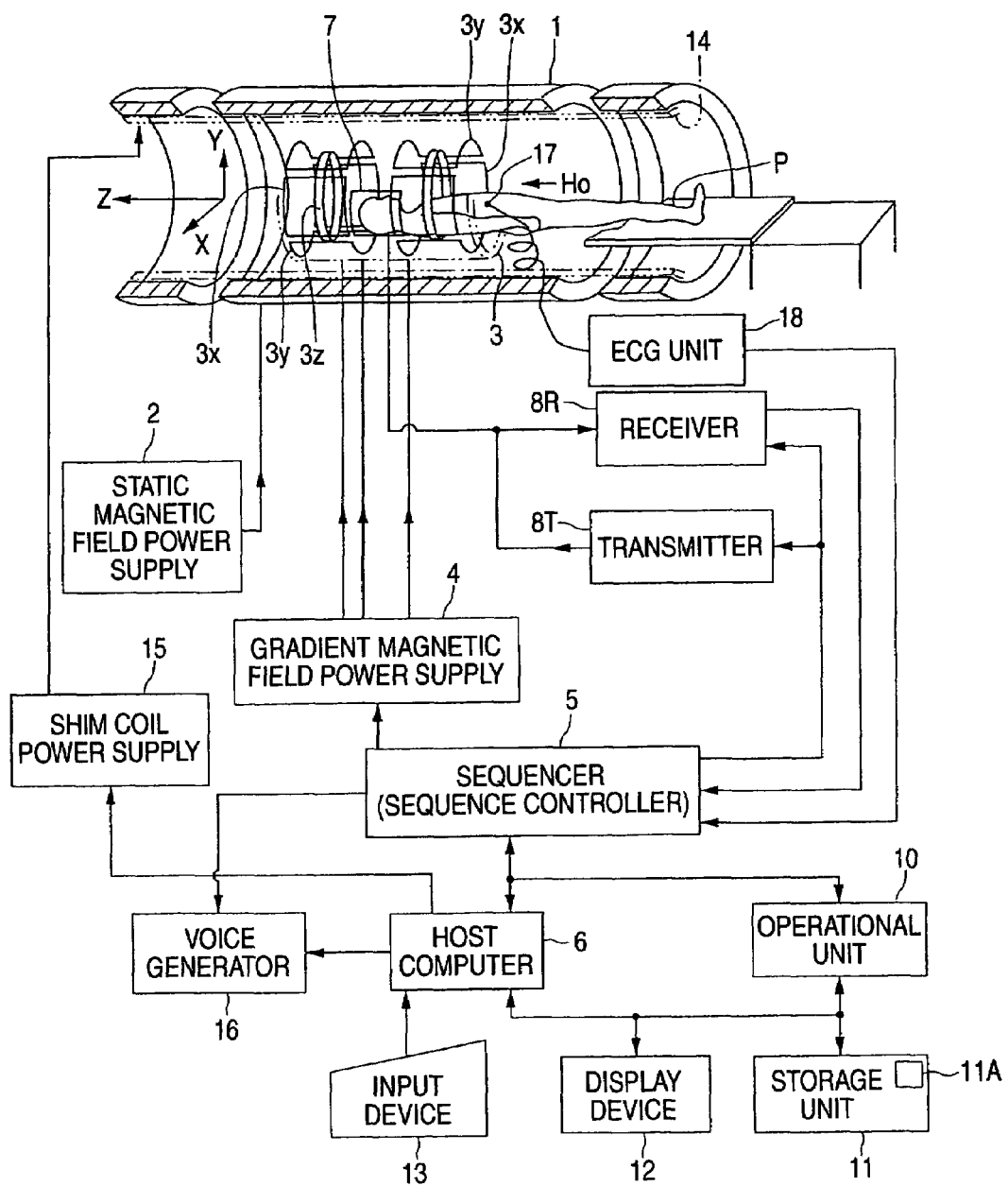
FIG. 4 is a functional block diagram showing one example of a schematic arrangement of a magnetic resonance imaging apparatus according to one embodiment of the invention.

FIG. 4 schematically shows an arrangement of a magnetic resonance imaging apparatus of this embodiment.

The magnetic resonance imaging apparatus includes a patient couch portion on which a subject P to be imaged (a person to be imaged) lies down, a static magnetic field generating portion for generating a static magnetic field, a gradient magnetic field generating portion for appending position information to the static magnetic field, a sending/receiving portion for sending and receiving high-frequency signals, a control and operational portion responsible for the control of an overall system and image reconstruction, an electrocardiogram measuring portion for measuring an ECG (electrocardiogram) signal as a signal representing cardiac temporal phases of the subject P to be imaged, and a breath-hold command portion for directing the subject P to be imaged to hold a breath.

The static magnetic field generating portion includes a magnet 1 of a superconducting type, for example, and a static magnetic field power supply 2 for supplying the magnet 1 with a current, and it generates a static magnetic field $h_0$ in the axial direction (Z-axis direction) of a cylindrical opening portion (diagnostic space) into which the subject P to be imaged is inserted. It should be noted that a shim coil 14 is provided to the static magnetic field generating portion. A current used to homogenize a static magnetic field is supplied to the shim coil 14 from a shim coil power supply 15 under the control of a host computer described below. A patient couch top of the patient couch portion on which the subject P to be imaged lies down can be inserted into the opening portion of the magnet 1 in such a manner that it can be pulled out.

The gradient magnetic field generating portion includes a gradient magnetic field coil unit 3 incorporated into the magnet 1. The gradient magnetic field coil unit 3 includes three sets (kinds) of x, y, z coils $3x$ through $3z$ used to generate gradient magnetic fields in the X-, Y-, and Z-directions that intersect at right angles with one another. The gradient magnetic field generating portion also includes a gradient magnetic field power supply 4 that supplies the x, y, and z coils $3x$ through $3z$ with a current. The gradient magnetic field power supply 4 supplies the x, y, and z coils $3x$ through $3z$ with a pulse current used to generate gradient magnetic fields under the control of a sequencer 5 described below.

By controlling a pulse current to be supplied to the x, y, and z coils $3x$ through $3z$ from the gradient magnetic field power supply 4, it is possible to set and change, as needed, the respective logical axial directions of a slicing direction gradient magnetic field Gs, a phase-encoding direction gradient magnetic field Ge, and a readout direction (frequency-encoding direction) gradient magnetic field Gr, intersecting at right angles with one another, by synthesizing the gradient magnetic fields in three physical axes in the X-, Y-, and Z-directions. The respective gradient magnetic fields in the slicing direction, the phase-encoding direction, and the readout direction are superimposed on the static magnetic field $h_0$.

The sending/receiving portion includes an RF coil 7 provided in close proximity to the subject P to be imaged in the diagnostic space inside the magnet 1, and a transmitter 8T and a receiver 8R both connected to the coil 7. The transmitter 8T and the receiver 8R operate under the control of the sequencer 5 described below. The transmitter 8T supplies the RF coil 7 with an RF current pulse at the Larmor frequency for inducing nuclear magnetic resonance (NMR). The receiver 8R takes in an MR signal (high-frequency signal) received at the RF coil 7, and applies various signal processing, such as pre-amplification, conversion into an intermediate frequency, phase detection, low-frequency amplification, and filtering, to the MR signal, after which it generates data (original data) of a digital quantity commensurate with the MR signal through analog-to-digital conversion.

Further, the control and operational portion includes the sequencer (also referred to as the sequence controller) 5, the host computer 6, an operational unit 10, a storage unit 11, a display device 12, an input device 13, and a voice generator 16. Of these components, the host computer 6 is furnished with a function of not only specifying pulse sequence information to the sequencer 5, but also managing operations of the entire apparatus, through procedures based on pre-stored software.

Figure 5:
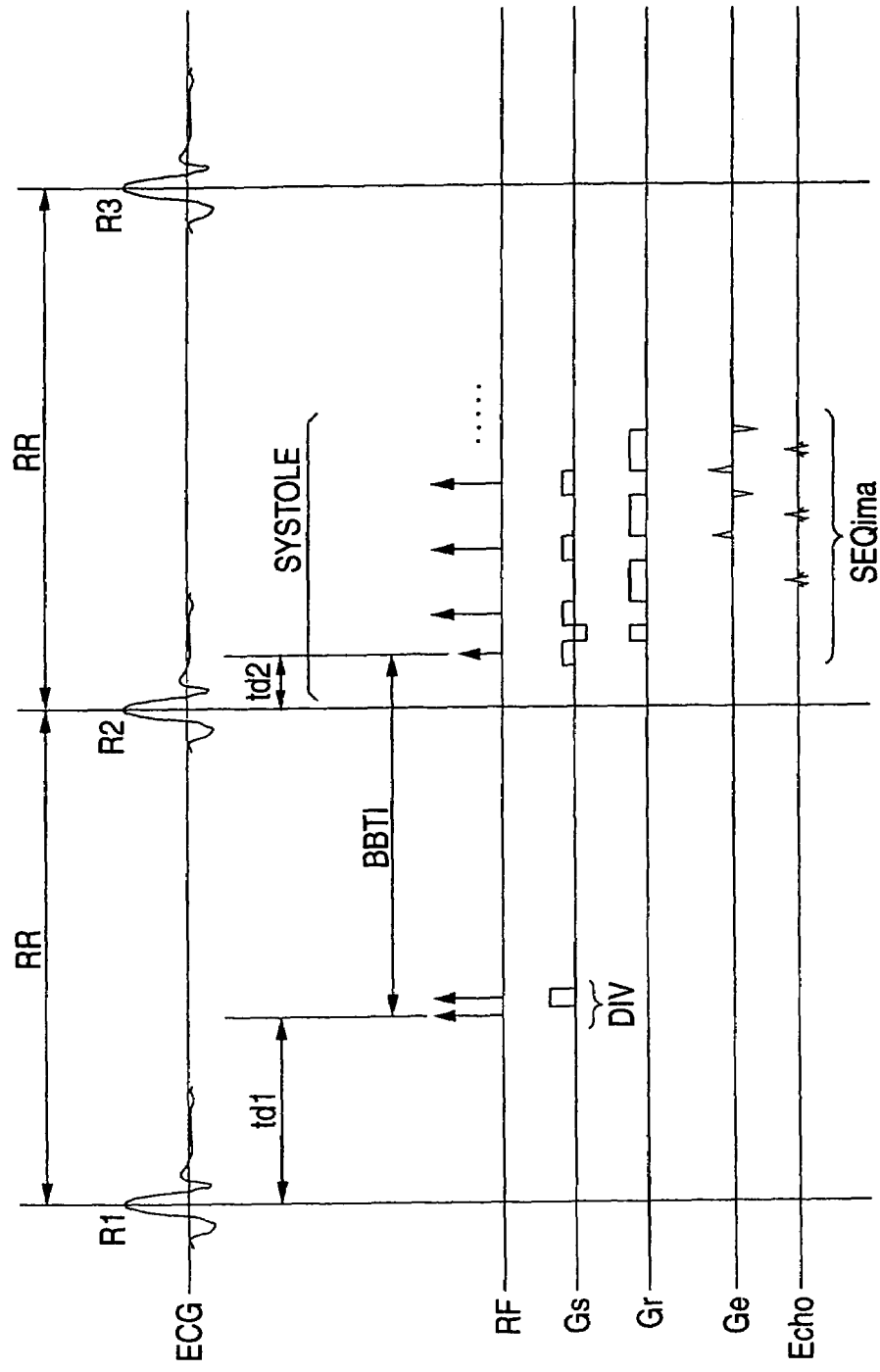
FIG. 5 illustrates a pulse sequence showing the black blood method used in the embodiment.

The host computer 6 performs scanning of MR imaging through the black blood method shown in FIG. 5 together with the cardiac synchronization method following a preparation work, such as scanning for positioning (not shown), and thereby acquires sets of echo data needed for image reconstruction. According to this black blood method, a double inversion pulse DIV as a pre-pulse for suppressing signals from blood is applied, and an imaging pulse train $SEQ_{ima}$ is then applied when a predetermined waiting time (the time at which the longitudinal magnetization of magnetized spins inverted by the double inversion pulse is reduced to or nearly to a null point) BBTI has elapsed since the double inversion pulse DIV was applied. Any pulse train, including the one based on the 2-D scanning or 3-D scanning FE (Field Echo), the SE (Spin Echo), the EPI (Echo Planar Imaging), etc. can be used as the imaging pulse train $SEQ_{ima}$.

In this black blood method, the characteristic corresponding to the invention is, as will be described below, that the cardiac synchronization is applied to the double inversion pulse DIV and the imaging pulse train $SEQ_{ima}$ individually.

The sequencer 5 includes a CPU and a memory, and is arranged in such a manner that it stores pulse sequence information sent from the host computer 6, and controls operations of the gradient magnetic field power supply 4, the transmitter 8T, and the receiver 8R according to this information while receiving digital data of an MR signal outputted from the receiver 8R, the data being transferred later to the operational unit 10. The pulse sequence information referred to herein means all the information needed to activate the gradient magnetic field power supply 4, the transmitter 8T, and the receiver 8R according to a series of pulse sequences, and for example, it includes information related to the strength, an application time, and an application timing of a pulse current to be applied to the x, y, and z coils $3x$ through $3z$.

The operational unit 10 receives raw data (also referred to as original data) of a digital quantity outputted from the receiver 8R through the sequencer 5, then maps the raw data in a Fourier space (a k-space or a frequency space) on the internal memory, and reconstructs the mapped raw data into image data in a real space through 2-D or 3-D Fourier transformation for each set. Also, the operational unit can perform synthesis (addition) processing, differential operation processing, etc. with respect to the image data when necessity arises.

The storage unit 11 can store computer programs necessary for the apparatus to perform signal control, data processing, and data computation, and reconstructed image data as well as image data to which the aforementioned synthesis processing or the differential processing has been applied. Hence, a recoding medium 11A loaded into the storage unit 11 also pre-stores an MR imaging program through the black blood method of the invention, which program is read out by the host computer 6 and the sequencer 5. The recording medium 11A can be a disc element such as an FD, a CD, and a hard disc, and various types of a semiconductor memory.

The display device 12 displays an image. Also, imaging conditions the operator desires, the pulse sequence information, parameters for the computation method, such as image fusion and differential processing, etc. are inputted into the host computer 6 through the input device 13.

Also, the voice generator 16 is provided as one component forming the breath-hold command portion. Information related to computation can be inputted into the host computer 6. Upon receipt of a command from the host computer 6, the voice generator 16 can utter voice messages instructing when to start breath holding and end breath holding.

Further, the electrocardiogram measuring portion includes an ECG sensor 17, attached to the surface of the body of the subject P to be imaged, for detecting an ECG (electrocardiogram) signal as a signal representing cardiac temporal phases, and an ECG unit 18 for processing the ECG signal and outputting a trigger signal in sync with, for example, a peak value of an R-wave to the sequencer 5. The trigger signal is used in the sequencer 5 when MR imaging of the black blood method is performed through the cardiac synchronization method.

In the arrangement of this embodiment, the ECG sensor 17 and the ECG unit 18 form acquiring means of the invention for acquiring a signal representing cardiac temporal phases. Also, the magnet 1, the gradient magnetic field coil unit 3, the gradient magnetic field power supply 4, the sequencer 5, the host computer 6, the RF coil 7, the transmitter 8T, and the storage unit 11 form major portions of pre-pulse applying means and scanning means of the invention. Further, the storage unit 11 includes memory means to be used as a recoding medium of the invention.

Figure 6:
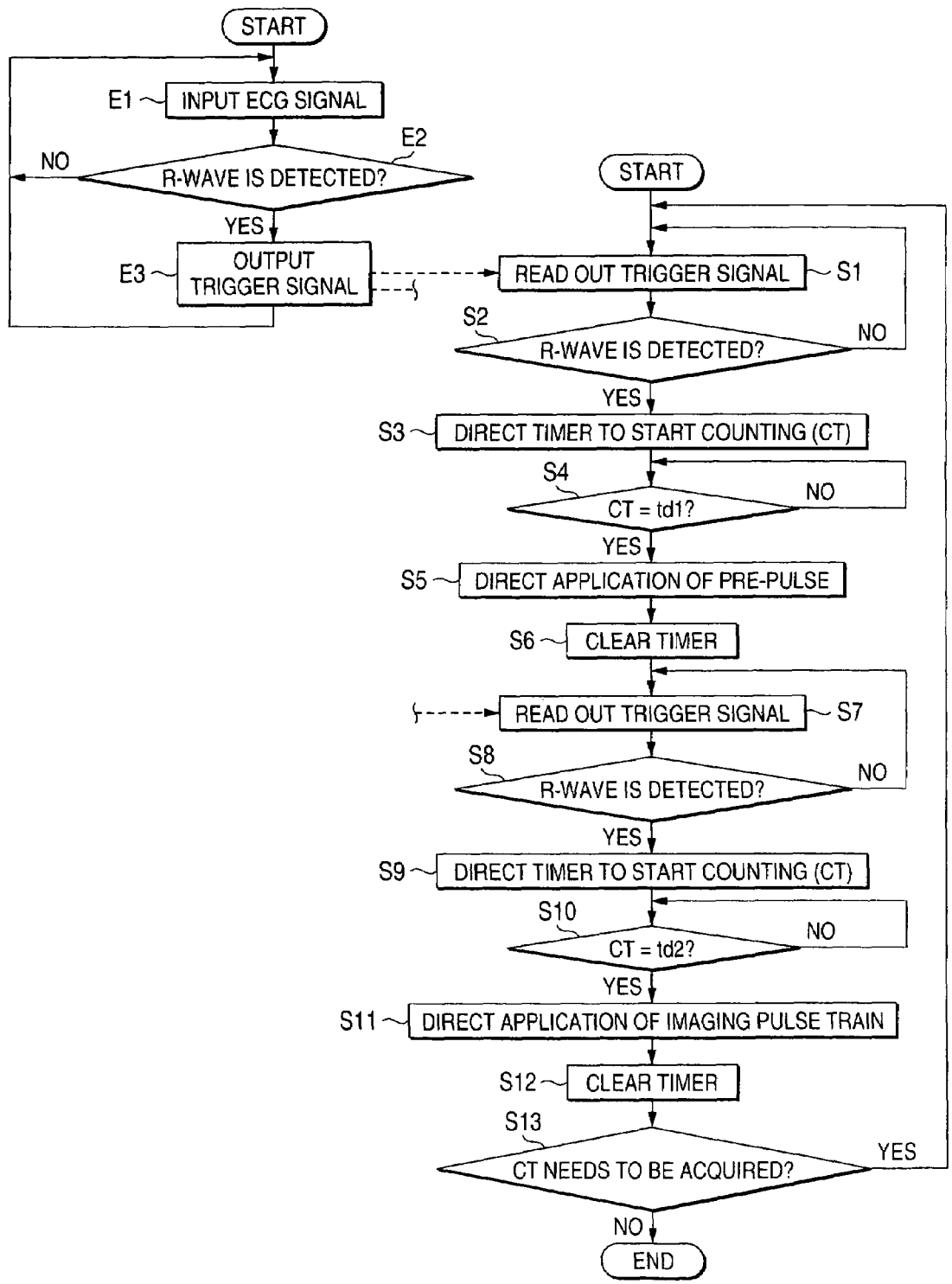
FIG. 6 illustrates a flowchart showing the summary of cardiac synchronization processing to perform the pulse sequence of FIG. 5.
Figure 7A:
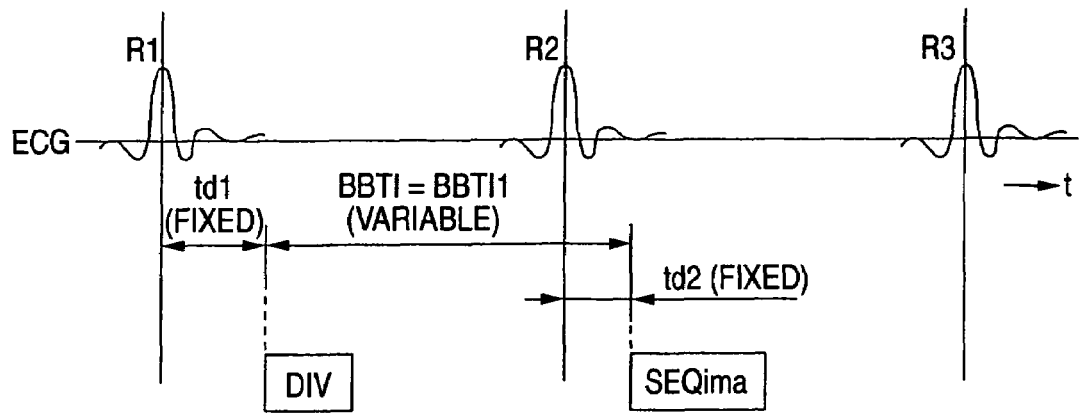
FIG. 7A and FIG. 7B are views used to explain a scheme to absorb a variance of a cardiac cycle.
Figure 7B:
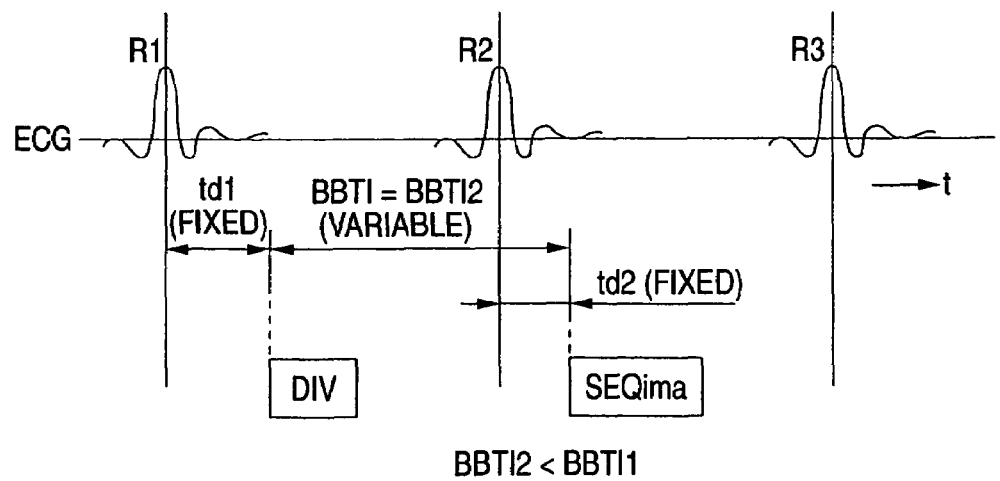

An operation of the magnetic resonance imaging apparatus of this embodiment will now be explained with reference to FIG. 5 through FIG. 7.

FIG. 5 shows a pulse sequence of the black blood method using a double inversion pulse, which is performed based on the cardiac synchronization method in this embodiment. The pulse sequence is performed by the sequencer 5 through the procedure of FIG. 6. This procedure is delivered to the sequencer 5 from the host computer 6 as the pulse sequence information.

The sequencer 5 first judges the arrival of the timing at which an R-wave of the ECG signal exhibits the peak value while trying to read out a trigger signal from the ECG unit 18 (Steps S1 and S2). This trigger signal is generated in the ECG unit 18. The ECG unit 18 repeats an operation that it receives the ECG signal from the ECG sensor 17, then detects the peak value of the R-wave, and outputs the trigger signal upon detection (Steps E1 through E3).

Upon detection of the appearance of the R-wave peak value, the sequencer 5 starts the time counting of a pre-installed software timer (Step S3). The R-wave detected in this instance is a first R-wave:R1 shown in FIG. 5.

Then, the sequencer 5 judges whether the counted value CT of the timer coincides with a predetermined delay time td1 from the R-wave shown in FIG. 5 (CT=td1) (Step S4). The delay time td1 is a time needed to apply cardiac synchronization to the double inversion pulse DIV as the pre-pulse, and corresponds to a first delay time of the invention. The delay time td1 is set in advance as will be described below.

In the case of NO at the judging step of Step S4, that is, when the counted time has not reached the delay time td1 yet, the time counting is continued; in the case of YES, the flow proceeds to the processing in the following step by deeming that the counted time has reached the delay time td1. That is, the start of application of the double inversion pulse DIV as the pre-pulse is directed by the sequencer 5 (Step S5). Then, the counted value of the aforementioned software timer is cleared (Step S6).

Subsequently, the sequencer 5 proceeds to the cardiac synchronization processing with respect to the imaging pulse train $SEQ_{ima}$. In other words, it tries to read out the trigger signal, and judges the arrival of the timing of the R-wave peak value when it succeeds in reading out the trigger signal in the same manner described above (Steps S7 and S8). The R-wave detected in this instance is an R-wave:R2 shown in FIG. 5.

In response to the detection of the R-wave peak value, time counting by the software timer is started, and whether the counted value CT=delay time td2 is judged in the same manner described above (Steps S9 and S10). The delay time td2 is a time needed to apply cardiac synchronization to the imaging pulse train $SEQ_{ima}$ with another R-wave (R2) different from that used for the pre-pulse. The delay time td2 is given in advance, so that data acquisition can be started, for example, at a desired timing in the diastole within one cardiac cycle.

For this reason, the application of the imaging pulse train $SEQ_{ima}$ shown in FIG. 5 is started when YES (CT=td2) is judged in Step S9 (Step S11). Then, the timer is cleared and the processing is returned to Step S1 in a case where the data acquisition through phase encoding is to be performed subsequently (Steps S12 and S13).

A setting method of the aforementioned delay time td1 of the double inversion pulse DIV will now be explained. The delay time td1 (fixed value) is computed in advance using the delay time td2 (fixed time) given as described above, the inversion time BBTI needed for the black blood method, and an average R-R space:RR of the ECG signal in accordance with an equation as follows:

$$td1 = RR + td2 - BBTI$$

Hence, scanning for MR imaging according to the black blood method shown in FIG. 5 is performed through the processing by the sequencer 5 described above.

That is, when the R-wave:R1 of the ECG signal at a given point appears, the double inversion pulse DIV is applied in sync with the pre-set delay time td1 from the time instant of the peak value. According to this pulse, an inversion pulse that gives rise to inversion excitation of the spins in the whole subject to be imaged without the application of the slicing direction gradient magnetic field Gs, and an inversion pulse that gives rise to inversion excitation of the spins in the imaging plane alone with application of the slicing direction gradient magnetic field Gs are applied successively.

After the application of the double inversion pulse DIV is started, the appearance of the following R-wave:R2 is waited. When the R-wave:R2 appears, the application of the imaging pulse train $SEQ_{ima}$ according to the fast SE method, for example, is started when the pre-set delay time td2 has elapsed since the time instant of the peak value. The echo signals respectively corresponding to a plurality of phase-encoding quantities are thereby acquired. These echo signals are converted into image data in the receiver 8R, and sent to the operational unit 10 for image reconstruction.

It is thus possible to acquire echo data while being hardly affected by the R-R space, that is, a variance of the cardiac cycle. For example, when a state of FIG. 7A with a large cardiac cycle changes to a state of FIG. 7B with a small cardiac cycle, the R-R space is shortened. However, such shortening is absorbed automatically in a reduction of the inversion time BBTI. Conversely, even when the cardiac cycle becomes larger, although the R-R space is enlarged, such enlargement is absorbed automatically in an extension of the inversion time BBTI. In the case of this black blood method, as long as the inversion time BBTI is varied within a range of the time width from 400 to 700 ms approximately, a difference of the suppressing effect of a blood signal is so small that influence given to the image quality is negligible.

As has been described, because a variance of the R-R space is absorbed by varying the inversion time BBTI within a necessary range, synchronization can be applied to the double inversion pulse DIV and the imaging pulse train $SEQ_{ima}$ individually with the pre-set delay times td1 and td2 of fixed values, respectively.

In other words, the imaging pulse train $SEQ_{ima}$ can be synchronized with R-waves independently of the double inversion pulse DIV. Hence, the scanning can be started at a desired timing in the systole within one cardiac cycle by taking the delay time td2 alone into account, which enables echo data acquisition in the systole. Accordingly, even in MR imaging using a pulse sequence having a long waiting time until the data acquisition after the pre-pulse was applied, such as the black blood method, echo acquisition can be performed without being affected by a variance of the cardiac cycle, thereby making the cardiac temporal phases at the time of acquisition regular. As a result, the conventional problem that the position of the cardiac muscle at the time of acquisition sways in each shot can be avoided. It is thus possible to provide a high-quality MR image in the systole stably in a reliable manner by reducing the artifacts.

Incidentally, the above description of the operation and the effect described above that a variance of the R-R space can be absorbed by varying the inversion time BBTI within a range of a necessary time (approximately 400 to 700 ms), and the following description will describe the reason more in detail.

The imaging method that applies a pre-pulse before the application of the imaging pulse train needed for imaging includes the inversion-recovery method in addition to the black blood method using the pre-pulse, such as the double inversion pulse. The inversion-recovery method is a generic name, and it includes sequences called the FLAIR method (suppressing CSF (Cerebral Spinal Fluid)) and the STIR method (suppressing fat) depending on a time until the application of the imaging pulse train is started after the inversion pulse was applied and the purpose of use of the inversion pulse.

In the case of the imaging method based on the inversion recovery (the FLAIR method and STIR method), a quantity of longitudinal magnetization of all the tissues having signal values on an image varies in response to a variance of time until the application of the imaging pulse train is started after the pre-pulse was applied, which influences the contrast of the entire image significantly. On the contrary, in the case of the black blood method, the tissues chiefly having the signal values on an image, such as the cardiac muscle and the chest wall, are subjected to inversion excitation from both the two inversion pulses as the pre-pulse (undergo inversion excitation twice). For this reason, even when there is a variance of a time until the application of the imaging pulse train is started after the pre-pulse was applied, the longitudinal magnetization having undergone the inversion excitation twice maintains most of the quantity at the time instant at which the application of the imaging pulse train is started. In other words, because a quantity of longitudinal magnetization close to the initial state can be maintained at the time instance at which the imaging is started, the signal values on the image cause a small variance. This allows for a margin when setting a time (the aforementioned inversion time BBTI) until the application of the imaging pulse train is started after the pre-pulse was applied.

Also, according to this black blood method, in regard to blood flowing into the field of view (for example, a slice), the signal value of the blood flow varies in response to a variance of the time until the application of the imaging pulse train is started after the pre-pulse was applied as with the conventional imaging method based on the inversion recovery. However, this variance is sufficiently small with respect to the aforementioned signal values of tissues, such as the cardiac muscle and chest wall.

In the case of the black blood method, even when there is a variance of approximately 10% in a time width until the application of the imaging pulse train is started after the pre-pulse was applied, the influence to the image quality hardly causes a problem.

As has been described, this black blood method is robust against a variance of the time until the application of the imaging pulse train is started after the pre-pulse was applied in comparison with the conventional imaging method based on the inversion recovery in terms of the quality of an entire image. Hence, a margin is allowed for the setting of the time (the aforementioned inversion time BBTI) until the application of the imaging pulse train is started after the pre-pulse was applied, and as is performed in the embodiment described above, it is possible to absorb a variance of the R-R space within a certain range.

The magnetic resonance imaging apparatus and the scanning synchronization method of the invention are not limited to the embodiment described above, and can be implemented in various manners. The following description will describe one example.

Figure 8:
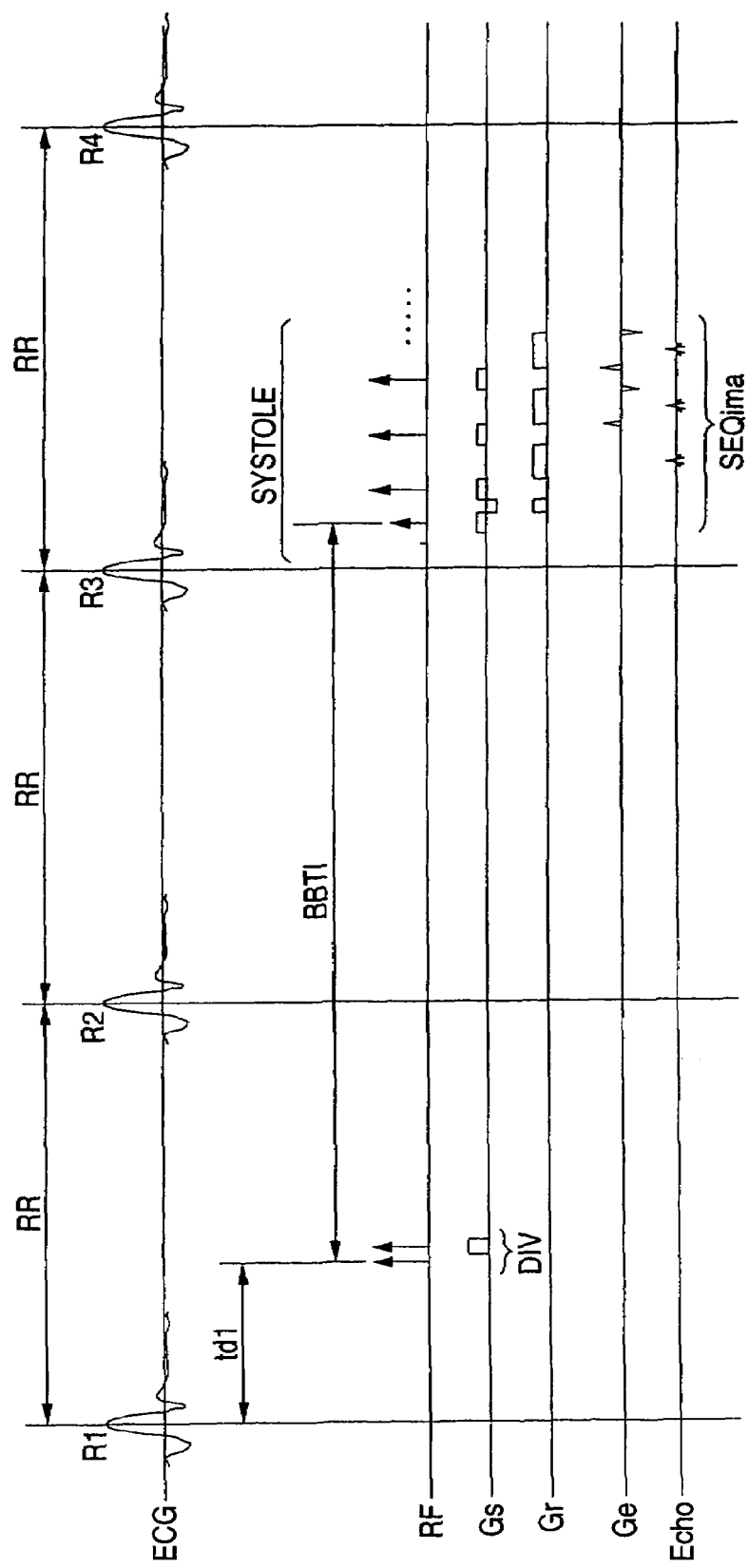
FIG. 8 illustrates a pulse sequence showing the black blood method used in a modified embodiment of the invention.

The embodiment above described the arrangement such that the double inversion pulse DIV and the imaging pulse train $SEQ_{ima}$ are synchronized with two different consecutive R-waves:R1 and R2, respectively. However, the invention is not necessarily limited to such an arrangement, and it may be arranged in such a manner that, for example, as shown in FIG. 8, after the double inversion pulse DIV is synchronized with the R-wave:R1, the imaging pulse train $SEQ_{ima}$ is synchronized with an R-wave:R3 by skipping one R-wave:R2. Two or more R-waves may be skipped. In order to achieve this, for example, the processing to count a desired number of R-waves is interposed between Steps S8 and S9 shown in FIG. 6, so that the flow proceeds to the processing shown in Step S9 when the counted number reaches the desired number. By arranging in this manner, it is possible to provide variations to the setting method of the inversion time BBTI in addition to the operation and the effect same as those described in the embodiment above.

Figure 9:
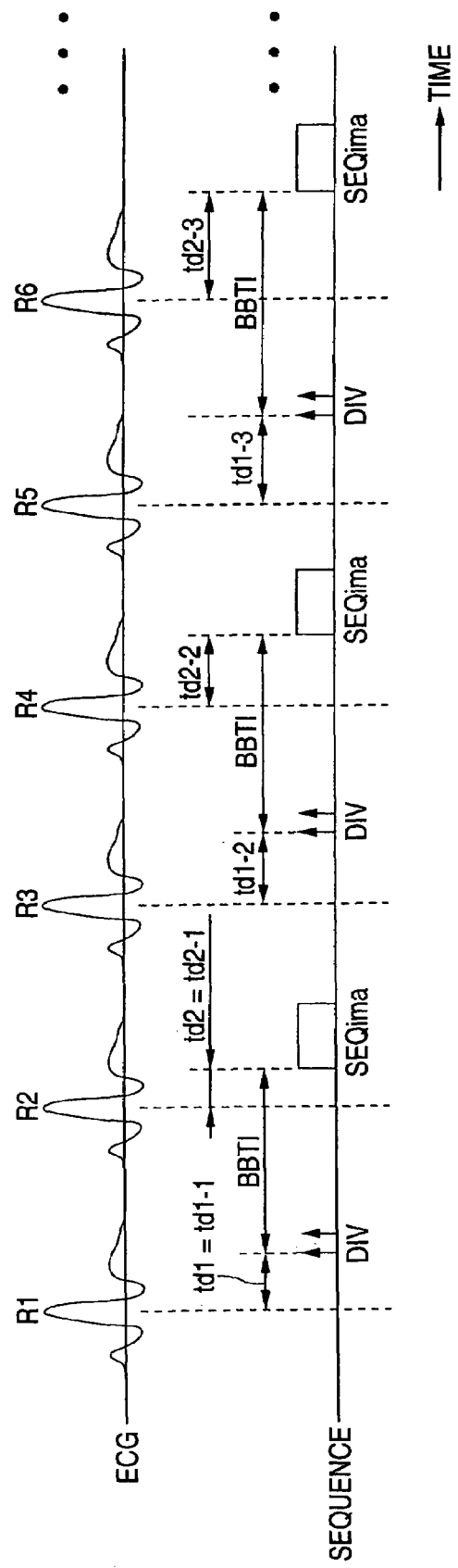
FIG. 9 illustrates a pulse sequence used to explain a cine mode imaging method according to still another modified embodiment of the invention.

Also, it is possible to apply the magnetic resonance imaging method of the invention to the cine mode imaging through the black blood method, which has been practically infeasible. FIG. 9 schematically shows a sequence for the method of the invention used in the cine mode imaging. As shown in this sequence, the delay time td2 of the imaging pulse train $SEQ_{ima}$ from the R-wave is changed successively to different values, td2=td2-1, td2-2, td2-3, and so forth, and imaging of, for example, a specific slice is performed in a plurality of temporal phases having different R-R spaces. The delay time td2 is first specified with desired values td2-1, td2-2, td2-3, and so forth, and computation is performed with respect to these specified values in accordance with the aforementioned computation equation (td1=RR+td2−BBTI). In other words, the delay times td1=td1-1, td1-2, td1-3, and so forth of the double inversion pulse DIV are found individually with the consideration given to the inversion time BBTI that is a variable value within a predetermined range and the R-R space that is used as the average value.

Further, the invention is not limited to the arrangements of the embodiment and the modified embodiment described above, and can be implemented in another embodiment without deviating the scope described in appended claims.

For example, the aforementioned detection method of a Signal representing the heart beats is not limited to the method of detecting an ECG signal, and a method of detecting a pulse wave, a method of using the strength of an MR signal itself, a method of making a detection through the use of a phase shift in an echo signal, a method of using a navigator echo, etc. may be used as occasion demands.

Also, the imaging sequence of the MR imaging to which the invention is applicable is not necessarily limited to the black blood method. The pre-pulse used in the imaging sequence is not limited to the aforementioned double inversion pulse, either. For example, although the purpose of use differs from that of the double inversion pulse, the pre-pulse may be a pre-saturation pulse using a single 90° pulse, or an inversion pulse using a single 180° pulse. Further, the MR imaging to which the invention is applied can be used for both the 2-D scanning and the 3-D scanning.

Further, the embodiments described above with reference to FIG. 5 and FIG. 8 described a case where the delay time td2 is set so that the start time of the imaging pulse train is in time for the systole to enable the imaging in the systole. However, the imaging method of the invention is not limited to this case. For example, by varying the delay time td2 to an adequate value, it is possible to make the start time of the imaging pulse train in time for the diastole of the cardiac cycle, which enables the imaging in the diastole.

INDUSTRIAL APPLICABILITY

The invention can exhibit its usefulness in the field of MR imaging using an imaging sequence in which a waiting time until the application of the imaging pulse train is started after the pre-pulse was applied is relatively long in comparison with the cardiac cycle as with the black blood method or the like. In other words, because echo acquisition can be performed without being affected by a variance of the cardiac cycle, it is possible to avoid an event that the position of the tissues, such as the cardiac muscle, at the time instant of acquisition sways in each shot. A high-quality MR image in the systole can be thus provided stably in a reliable manner by reducing the artifacts, which in turn makes an extremely significant contribution in the field of the medical image diagnosis.

The invention claimed is:

1. A magnetic resonance imaging apparatus comprising:
an input unit configured to input a signal representing cardiac temporal phases of said subject to be imaged;
a pre-pulse applying unit configured to apply a pre-pulse to the subject;
a scanning unit configured to perform a scan applying an imaging pulse to a desired region of the subject after application of the pre-pulse; and
a control unit configured to control said pre-pulse applying unit to apply the pre-pulse using a specific waveform representing a temporal phase of a first cardiac cycle in a signal representing temporal phases of plural cardiac cycles as a first trigger and to control said scanning unit to apply the imaging pulse using a specific waveform representing a cardiac temporal phase of a second cardiac cycle as a second trigger so as to make a time interval from the specific waveform representing the cardiac temporal phase of the second cardiac cycle to application of the imaging pulse a fixed value by changing a time interval from the pre-pulse to the imaging pulse so as to be reduced when the first cardiac cycle is larger than the second cardiac cycle and be enlarged when the first cardiac cycle is shorter than the second cardiac cycle, the second cardiac cycle being later than the cardiac cycle by at least one cardiac cycle.

2. The magnetic resonance imaging apparatus according to claim 1, wherein said pre-pulse is a double inversion pulse that forms part of a pulse sequence through a black blood method.

3. The magnetic resonance imaging apparatus according to claim 1, wherein said signal representing the cardiac temporal phases is an ECG signal, and said specific waveform is an R-wave of said ECG signal.

4. The magnetic resonance imaging apparatus according to claim 1, wherein the second cardiac cycle is later than the first cardiac cycle by one cardiac cycle.

5. The magnetic resonance imaging apparatus according to claim 1, wherein the interval between said first and second cardiac cycle is two cardiac cycles.

6. The magnetic resonance imaging apparatus according to claim 1, wherein a time interval from application of said pre-pulse to application of said imaging pulse is long enough to account for at least approximately a half of one cycle of heart beat.

7. The magnetic resonance imaging apparatus according to claim 1, wherein a first delay time from the first trigger to the pre-pulse is a time calculated using a second delay time from the second trigger to the imaging pulse, a value of a time interval from application of said pre-pulse to application of said imaging pulse, and an average cycle of heart beat.

8. A scanning synchronization method of magnetic resonance imaging comprising:
   inputting a signal representing cardiac temporal phases of plural cardiac cycles of a subject to be imaged;
   applying a pre-pulse to the subject;
   performing scanning by applying an imaging pulse to a desired region of the subject after application of the pre-pulse; and
   controlling the pre-pulse using a specific waveform of a signal representing a cardiac temporal phase of a first cardiac cycle as a first trigger and controlling application of the imaging pulse using a specific waveform of a signal representing a cardiac temporal phase of a second cardiac cycle as a second trigger so as to make a time interval from the specific waveform representing the cardiac temporal phase of the second cardiac cycle to application of the imaging pulse a fixed value by changing a time interval from the pre-pulse to the imaging pulse so as to be reduced when the first cardiac cycle is larger than the second cardiac cycle and be enlarged when the first cardiac cycle is shorter than the second cardiac cycle, the second cardiac cycle being later than the first cardiac cycle by at least one cardiac cycle.

9. The scanning synchronization method according to claim 8, wherein said pre-pulse is a double inversion pulse that forms part of a pulse sequence through a black blood method.

10. The scanning synchronization method according to claim 8, wherein said signal representing the cardiac temporal phases is an ECG signal, and said specific waveform is an R-wave of said ECG signal.

11. The scanning synchronization method according to claim 8, wherein the interval between said first and second cardiac cycles is one cardiac cycle.

12. The scanning synchronization method according to claim 8, wherein the interval between said first and second cardiac cycles is two cardiac cycles.

13. The scanning synchronization method according to claim 8, wherein a time interval from application of said pre-pulse to application of said imaging pulse is long enough to account for at least approximately a half of one cycle of heart beat.

14. The scanning synchronization method according to claim 8, wherein a first delay from the first trigger to the pre-pulse is a time calculated using second delay time from the second trigger to the imaging pulse, a value of a time interval from application of said pre-pulse to application of said imaging pulse, and an average cycle of heart beat.

15. A computer-readable recording medium used for magnetic resonance imaging, said recording medium recording a program that causes a computer to perform:
   a function of inputting a signal representing cardiac temporal phases of plural cardiac cycles of a subject to be imaged;
   a function of applying a pre-pulse to be applied to the subject;
   a function of applying an imaging pulse to a desired region of the subject after application of the pre-pulse; and
   a function of controlling application of the pre-pulse using a specific waveform of a signal representing a cardiac temporal phase of a first cardiac cycle as a first trigger and controlling application of the imaging pulse using a specific waveform of a signal representing a cardiac temporal phase of a second cardiac cycle as a second trigger so as to make a time interval from the specific waveform representing the cardiac temporal phase of the second cardiac cycle to application of the imaging pulse a fixed value by changing a time interval from the pre-pulse to the imaging pulse so as to be reduced when the first cardiac cycle is larger than the second cardiac cycle and be enlarged when the first cardiac cycle is shorter than the second cardiac cycle, the second cardiac cycle being later than the first cardiac cycle by at least one cardiac cycle.

16. A magnetic resonance imaging apparatus comprising:
   an input unit configured to input a signal representing cardiac temporal phases of plural cardiac cycles of a subject to be imaged;
   a first detecting unit configured to detect a first timing on the basis of the signal;
   a pre-pulse applying unit configured to apply a pre-pulse to the subject in sync with the first timing with a first delay time by using a first trigger;
   a second detecting unit configured to detect a second timing on the basis of the signal, the second timing being at least one cardiac cycle later than the first timing; and
   a scanning unit configured to perform a scan by applying an imaging pulse to a desired region of the subject in sync with the second timing with a second delay time by using a second trigger making the second delay time a fixed value by changing a time interval from the pre-pulse to the imaging pulse so as to be reduced when the first cardiac cycle is larger than the second cardiac cycle and be enlarged when the first cardiac cycle is shorter than the second cardiac cycle.

17. The magnetic resonance imaging apparatus according to claim 16, wherein said pre-pulse is a double inversion pulse that forms part of a pulse sequence on a black blood method.

18. The magnetic resonance imaging apparatus according to claim 16, wherein said signal representing the cardiac temporal phases is an EGG signal and each of the first and second timings is a timing at which an R-wave of said EGG signal appears.

19. The magnetic resonance imaging apparatus according to claim 16, wherein the second timing is a timing at which one cardiac cycle of the subject has elapsed from the first timing.

20. The magnetic resonance imaging apparatus according to claim 16, wherein the second timing is a timing at which two cardiac cycles of the subject have elapsed from the first timing.

21. The magnetic resonance imaging apparatus according to claim 16, wherein the first and second delay times are set such that a waiting time interval from application of said pre-pulse to application start of said imaging pulse is long enough to account for at least approximately a half of one cycle of heart beat of the subject.

22. A scanning synchronization method of magnetic resonance imaging comprising:
   inputting a signal representing cardiac temporal phases of plural cardiac cycles of a subject to be imaged;
   detecting a first timing on the basis of the signal;
   applying a pre-pulse to the subject in sync with the first timing with a first delay time by using a first trigger;
   subsequently detecting a second timing on the basis of the signal, the second timing being at least one cardiac cycle later than the first timing; and
   performing scanning by applying an imaging pulse to a desired region of the subject in sync with the second timing with a second delay time by using a second trigger making the second delay time constant by changing a time interval from the pre-pulse to the imaging pulse so as to be reduced when the first cardiac cycle is larger than the second cardiac cycle and be enlarged when the first cardiac cycle is shorter than the second cardiac cycle.

23. The scanning synchronization method according to claim 22, wherein said pre-pulse is a double inversion pulse that forms part of a pulse sequence on a black blood method.

24. The scanning synchronization method according to claim 22, wherein said signal representing the cardiac temporal phases is an EGG signal, and each of the first and second timings is a timing at which an R-wave of said EGG signal appears.

25. The scanning synchronization method according to claim 22, wherein the second timing is a timing at which two cardiac cycles of the subject have elapsed from the first timing.

26. The scanning synchronization method according to claim 22, wherein the first and second delay times are set such that a waiting time interval from application of said pre-pulse to application start of said imaging pulse is long enough to account for at least approximately a half of one cycle of heart beat of the subject.

27. The scanning synchronization method according to claim 22, wherein said first delay time is a time interval calculated using said second delay time, a desired value of the waiting time interval and an average cycle of heart beat.

* * * * *